(12) United States Patent
Nishikawa et al.

(10) Patent No.: US 11,906,410 B2
(45) Date of Patent: Feb. 20, 2024

(54) CELL INSPECTION DEVICE AND CELL INSPECTION METHOD

(71) Applicant: OLYMPUS CORPORATION, Tokyo (JP)

(72) Inventors: Kazutaka Nishikawa, Tokyo (JP); Jun Funazaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 714 days.

(21) Appl. No.: 17/135,369

(22) Filed: Dec. 28, 2020

(65) Prior Publication Data

US 2021/0116339 A1    Apr. 22, 2021

Related U.S. Application Data (63) Continuation of application No. PCT/JP2018/025360, filed on Jul. 4, 2018.

(51) Int. Cl.
| | | |
|---|---|---|
| *G01N 1/40* | (2006.01) | |
| *C12Q 1/04* | (2006.01) | |
| *C12Q 1/24* | (2006.01) | |
| *G01N 1/30* | (2006.01) | |

(52) U.S. Cl.
CPC ............ *G01N 1/4077* (2013.01); *C12Q 1/04* (2013.01); *C12Q 1/24* (2013.01); *G01N 1/30* (2013.01); *G01N 2001/4088* (2013.01)

(58) Field of Classification Search
CPC ...... G01N 1/4077; G01N 1/30; G01N 1/2813; G01N 1/312; G01N 15/0625; G01N 2001/4088; G01N 2015/0065; G02B 21/24; C12Q 1/04; C12Q 1/24

See application file for complete search history.

(56) References Cited

U.S. PATENT DOCUMENTS

| | | | |
|---|---|---|---|
| 6,268,959 B1 | 7/2001 | Kawahito | |
| 9,057,064 B1 * | 6/2015 | Dyer | ................. C12N 15/101 |
| 2009/0000793 A1 | 1/2009 | Chen et al. | |
| 2009/0007937 A1 * | 1/2009 | Chen | ................. B01L 3/502 |
| | | | 134/10 |

(Continued)

FOREIGN PATENT DOCUMENTS

| | | |
|---|---|---|
| JP | 06-213789 A | 8/1994 |
| JP | 2001-066516 A | 3/2001 |

(Continued)

OTHER PUBLICATIONS

International Search Report dated Aug. 21, 2018 issued in PCT/JP2018/025360.

*Primary Examiner* — Michael L Hobbs
(74) *Attorney, Agent, or Firm* — Scully, Scott, Murphy & Presser, P.C.

(57) ABSTRACT

A cell inspection method includes a concentrate production step, a staining step, a cell precipitation step, and an observation step. In the concentrate production step, the cell concentrate is produced by causing an inner cylinder which has a filter provided on a bottom surface to enter from the bottom surface side into the through hole of the outer cylinder and bringing the inner cylinder closer to the slide, the inner cylinder having an internal space, and in the observation step, observation is performed in a state where the inner cylinder is entered into the outer cylinder.

17 Claims, 12 Drawing Sheets

(56) References Cited

U.S. PATENT DOCUMENTS

2013/0029407 A1  1/2013  Terazono et al.

FOREIGN PATENT DOCUMENTS

| | | |
|---|---|---|
| JP | 2003-529768 A | 10/2003 |
| JP | 2009-011319 A | 1/2009 |
| JP | 2009-282198 A | 12/2009 |
| JP | 2010-127807 A | 6/2010 |
| JP | 2014-524020 A | 9/2014 |
| JP | 2017-055758 A | 3/2017 |
| WO | 01/75446 A1 | 10/2001 |
| WO | 2011/105507 A1 | 9/2011 |
| WO | 2013/000897 A1 | 1/2013 |

* cited by examiner

CELL INSPECTION DEVICE AND CELL INSPECTION METHOD

This application is a continuation application based on PCT/JP2018/025360, filed on Jul. 4, 2018. The content of the Japanese Patent Application and the PCT Application is incorporated herein by reference.

BACKGROUND OF THE INVENTION

Field of the Invention

The present invention relates to a cell inspection device and a cell inspection method.

Description of Related Art

Rapid on-site evaluation (hereinafter referred to as ROSE) is known as a method for rapidly diagnosing cells collected with a puncture needle or the like while observing the cells with an ultrasound endoscope. In general ROSE, a cell suspension is produced by diluting the cells collected by the puncture needle with a cell preservation solution. After the cells are sampled by filtering the cell suspension with a filter, the cells are observed by a microscope. By virtue of ROSE, it is possible to determine whether or not required cells have been collected in a location where the cells are collected.

In a case where ROSE is not used, the cells collected by the puncture needle or the like are transferred to an inspection location different from the location where the cells are collected, and an inspection such as a pathological diagnosis is performed. As a result, in a case where the required cells have not been collected, it is necessary to collect the cells again. In the inspection using ROSE, since it is possible to determine whether or not the required cells have been collected on the spot where the cells have been collected, the collection of the cells can be easily added. Therefore, since ROSE can reduce the re-inspection rate, it is desired to carry out ROSE in each facility.

In the production of cell samples, a method for precipitating cells on a slide is known (refer to, for example, Japanese Unexamined Patent Application, First Publication 6-213789). Japanese Unexamined Patent Application, First Publication 6-213789 includes a hollow tube having a space inside, a microscope slide on which the hollow tube is mounted, and a base plate having formed therein a recess in which the microscope slide fits.

The microscope slide is fit into the recess of the base plate and the hollow tube is mounted on the microscope slide. A predetermined sample cell suspension is put into the space of the hollow tube and a person waits for the cells to precipitate due to gravity. Once the cells have precipitated on the microscope slide, the supernatant is taken out by suction, the cells are stained, and then the cells on the microscope slide are observed.

SUMMARY OF THE INVENTION

A cell inspection method for inspecting cells contained in a cell suspension by using a light source and an observation unit, the cell inspection method comprising: a concentrate production step of injecting the cell suspension into a chamber formed of an outer cylinder and a slide, and producing a cell concentrate, the outer cylinder having a through hole; a staining step of staining the cells on the slide; a cell precipitation step of precipitating the cells on the slide; and an observation step of observing the cells on the slide by the observation unit while illuminating the cells with the light source. In the concentrate production step, the cell concentrate is produced by causing an inner cylinder which has a filter provided on a bottom surface to enter from the bottom surface side into the through hole of the outer cylinder and bringing the inner cylinder closer to the slide, the inner cylinder having an internal space, and in the observation step, observation is performed in a state where the inner cylinder is entered into the outer cylinder.

In the staining step, the cells in the cell concentrate may be stained by injecting a staining solution into a space surrounded by the inner cylinder and the through hole of the outer cylinder.

The cell inspection method further may include a suction step of suctioning the staining solution in the internal space of the inner cylinder.

In the observation step, the filter of the inner cylinder may be placed at a distance from the slide.

In the observation step, the filter of the inner cylinder may be brought into contact with the slide.

In at least one of the concentrate production step and the staining step, the inner cylinder may be advanced and retracted in a longitudinal direction of the outer cylinder.

A cell inspection device that inspects cells contained in a cell suspension includes an outer cylinder which has a through hole and is arranged on the slide, the through hole of the outer cylinder and a slide forming a chamber, an inner cylinder that has an internal space, and is capable of being inserted into the through hole of the outer cylinder, a filter being provided on a bottom surface of the inner cylinder, a staining solution injector which injects a staining solution into the chamber in a state where the cells is concentrated, and an observation unit that is provided on a side opposite to a side in which the outer cylinder is provided with respect to the slide. In a state where the cell suspension is accommodated in the chamber, a concentration of the cells is executed in a state where the inner cylinder is entered from the bottom surface side into the through hole of the outer cylinder and approaches the slide and in a state where the cells are stained by the staining solution and precipitated on the slide, observation of the cells by the observation unit is capable of being executed in a state where the inner cylinder is kept as entering into the outer cylinder.

A cell inspection device that inspects cells contained in cell suspension includes a base plate, an outer cylinder that has a through hole and is arranged on a slide, an inner cylinder that has an internal space, and is capable of being inserted into the through hole of the outer cylinder, a filter being provided on a bottom surface of the inner cylinder, and a light source, and an observation unit that is provided opposite to a side in which the outer cylinder is provided with respect to the slide. A chamber for injecting the cell suspension is formed by the slide and the through hole of the outer cylinder, the base plate has an observation hole formed therein and has a depression on which the slide is mounted, and the filter of the inner cylinder is made of a light-transmitting material, and the light source illuminates cells in the chamber in a state where the inner cylinder is entered into the outer cylinder.

A communication hole may be provided in a side wall of the outer cylinder, and the through hole of the outer cylinder and an outside may communicate with each other through the communication hole.

The observation unit may be capable of being inserted into the observation hole.

The cell inspection device further may include a light source which is capable of being inserted into the internal space of the inner cylinder.

The filter may be made of a material having a refractive index higher than that of the cell suspension.

The filter may have a pore size smaller than that of the cells.

DETAILED DESCRIPTION OF THE INVENTION

Embodiment

A cell inspection device according to an embodiment of the present invention will be described with reference to FIGS. 1 to 16.

Figure 1:
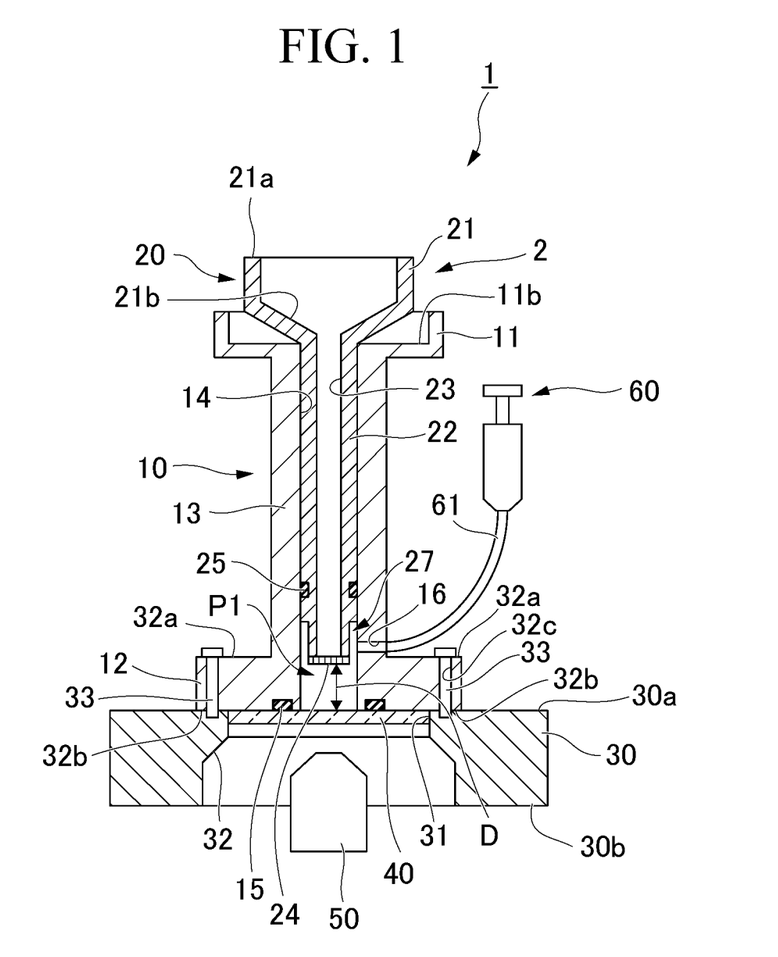
FIG. 1 is an overall view illustrating a cell inspection device according to an embodiment of the present invention.

The cell inspection device 1 is a device that observes cells contained in a cell suspension. In addition, the cells may contain bacteria. As illustrated in FIG. 1, the cell inspection device 1 includes an outer cylinder 10 and an inner cylinder 20 placed on a base plate 30, and an observation unit 50.

Figure 2:
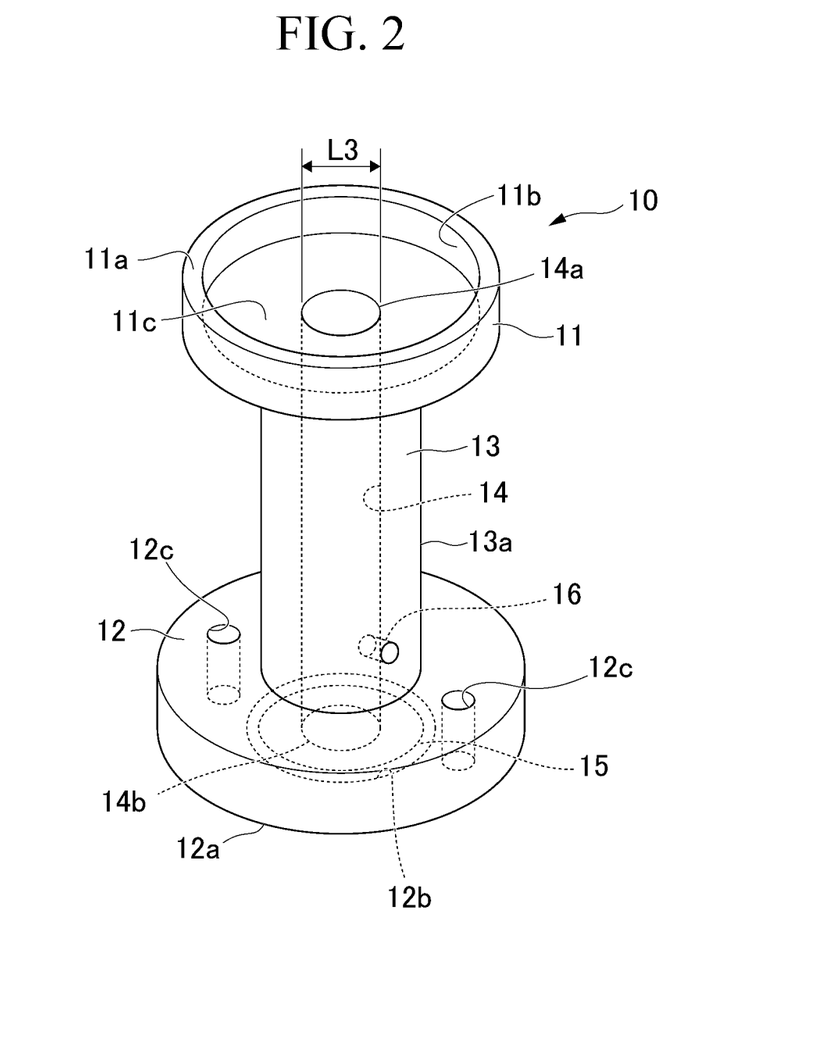
FIG. 2 is a perspective view illustrating an outer cylinder of FIG. 1.

As illustrated in FIG. 2, the outer cylinder 10 includes an upper part 11, a bottom part 12, and a cylindrical tubular part 13 that connects the upper part 11 and the bottom part 12, in a longitudinal direction of the outer cylinder 10. A through hole 14 is formed in the longitudinal direction of the outer cylinder 10 in the outer cylinder 10. A communication hole 16 that allows the through hole 14 of the outer cylinder 10 to communicate with the outside is formed in an outer wall (side wall) 13a of the tubular part 13.

The upper part 11 has an enlarged diameter in a direction perpendicular to the longitudinal direction of the outer cylinder 10. The upper part 11 has formed therein a recess 11b that opens toward an upper surface 11a of the upper part 11. The cell suspension is injected from the recess 11b. A first end 14a of the through hole 14 opens to a bottom surface 11c of the recess 11b, and a second end 14b of the through hole 14 opens to a bottom surface 12a of the bottom part 12. Accordingly, the through hole 14 penetrates from the recess 11b of the upper part 11 to the bottom surface 12a of the bottom part 12.

The bottom part 12 has an enlarged diameter in a direction perpendicular to the longitudinal direction of the outer cylinder 10. An annular groove 12b is provided on the bottom surface 12a of the bottom part 12. An O-ring 15 formed of an elastic member such as rubber is disposed in the groove 12b. A screw hole 12c through which a screw 33 described below can be inserted is formed in the bottom part 12 so as to penetrate in a thickness direction of the bottom part 12. A pair of the screw holes 12c are provided symmetrically with a longitudinal axis of the outer cylinder 10 interposed therebetween.

Figure 3:
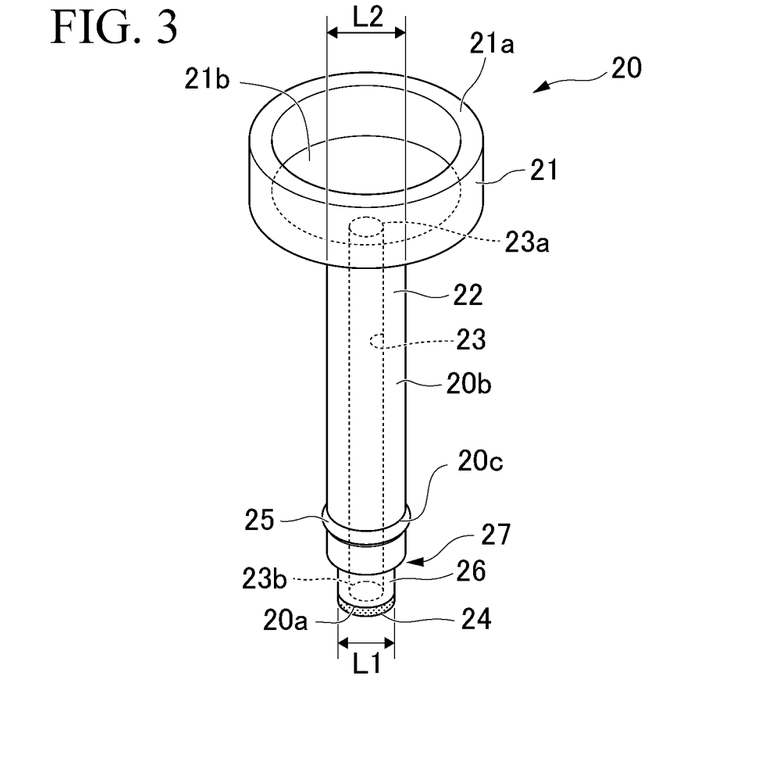
FIG. 3 is a perspective view illustrating an inner cylinder of FIG. 1.

As illustrated in FIG. 3, the inner cylinder 20 includes an upper part 21 and a cylindrical tubular part 22.

The upper part 21 has an enlarged diameter in the direction perpendicular to the longitudinal direction of the outer cylinder 10. The upper part 21 has formed therein a recess 21b that opens toward an upper surface 21a of the upper part 21. As illustrated in FIG. 1, the recess 21b is reduced in diameter toward the tubular part 22.

As illustrated in FIG. 3, an internal space 23 is formed along the longitudinal direction of the tubular part 22 in the tubular part 22. A first end 23a of the internal space 23 opens to the recess 21b, and the second end 23b of the internal space 23 opens to a bottom surface 20a of the inner cylinder 20. Accordingly, the internal space 23 penetrates from the upper part 21 to the bottom surface 20a of the tubular part 22.

A filter 24 is adhered to the bottom surface 20a of the tubular part 22. The filter 24 covers the bottom surface 20a of the tubular part 22. The filter 24 has a pore size smaller than that of cells. The filter material of the filter 24 is not particularly limited but is made of, for example, a woven fabric or a non-woven fabric. The filter 24 is made of a material having light transmittance. The filter 24 is made of a material having a refractive index higher than the refractive index of the cell suspension.

An annular groove 20c is provided on the outer surface 20b of the tubular part 22. An O-ring 25 formed of an elastic member such as rubber is disposed in the groove 20c. The O-ring 25 protrudes radially outward from the tubular part 22.

An outer diameter L1 of a tip part 26 (a side opposite to the side where the upper part 21 is placed) of the tubular part 22 in the direction perpendicular to a longitudinal axis direction of the tubular part 22 is smaller than an outer diameter L2 of the tubular part 22 in the direction perpendicular to the direction of the longitudinal axis of the tubular part 22. Accordingly, a step part 27 is formed at the tip part 26 of the tubular part 22.

Figure 4:
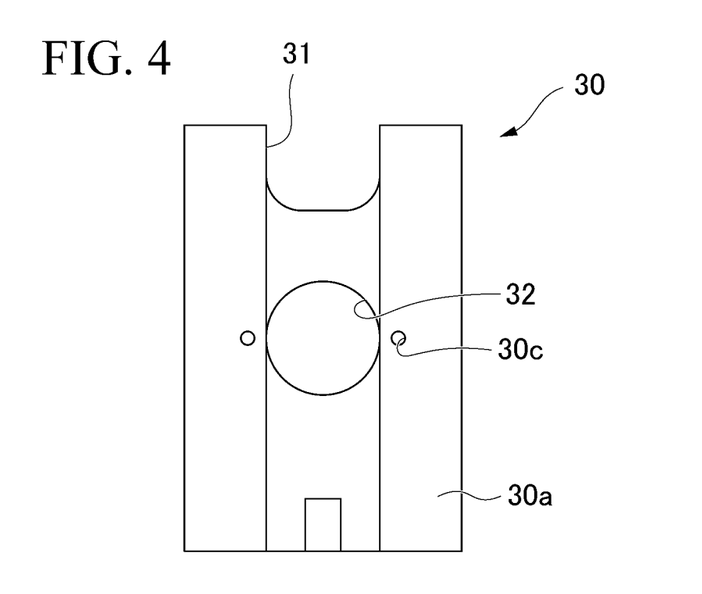
FIG. 4 is a top view illustrating a base plate of FIG. 1.

As illustrated in FIG. 1, the outer cylinder 10 is attached to the base plate 30 fitted to a stage (not illustrated) of a generally used microscope. As illustrated in FIG. 4, the base plate 30 includes a depression 31 and an observation hole (through hole) 32.

The base plate 30 has formed therein a screw hole 30c that penetrate in the thickness direction (from an upper surface 30a to a lower surface 30b). The depression 31 has a substantially oblong shape, and a slide 40 is mounted on the depression 31. The observation hole 32 is formed in the depression 31, and as illustrated in FIG. 1, penetrates from the depression 31 to the lower surface 30b. The observation unit 50 is capable of entering the observation hole 32.

Figure 5:
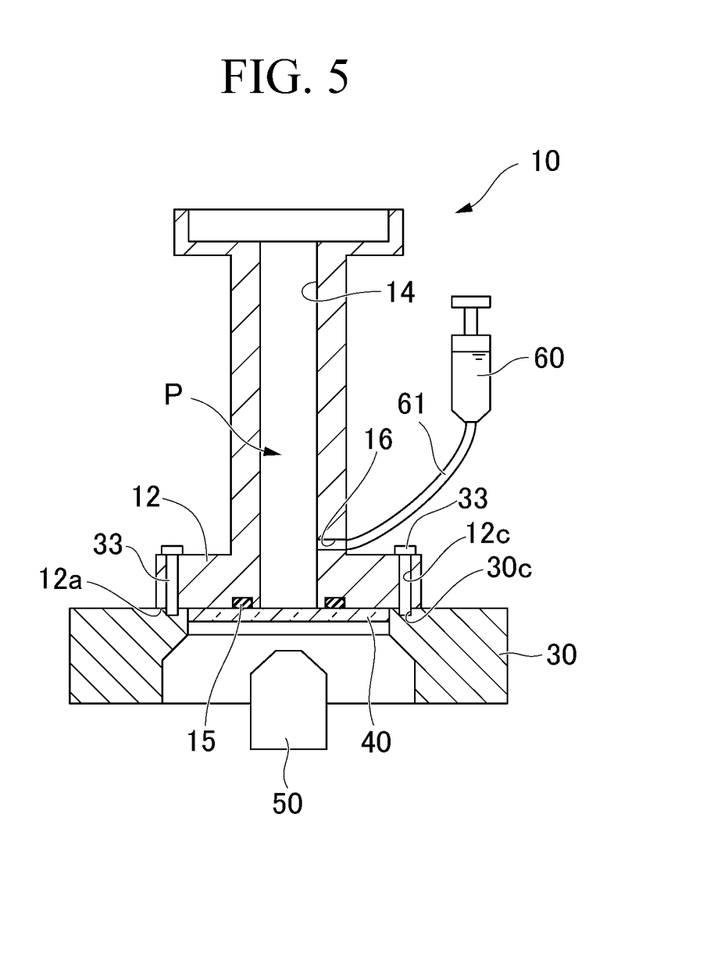
FIG. 5 is a cross-sectional view of main parts illustrating a state in which the outer cylinder is attached to the base plate of FIG. 1.

As illustrated in FIG. 5, the outer cylinder 10 is placed on the slide 40 such that the bottom surface 12a of the bottom part 12 of the outer cylinder 10 comes into contact with the slide 40. Accordingly, a chamber P is formed by the through hole 14 of the outer cylinder 10 and the slide 40. A cell suspension is injected into the chamber P. The outer cylinder 10 and the base plate 30 are fixed by inserting the screw 33 into the screw hole 12c and the screw hole 30c. The liquid tightness between the through hole 14 of the outer cylinder 10 and the slide 40 can be ensured by the O-ring 15 in a state in which the outer cylinder 10 is fixed to the base plate 30. That is, the cell suspension injected into the chamber P does not leak out of the chamber P from the bottom surface 12a of the bottom part 12 of the outer cylinder 10.

A syringe (staining solution injector) 60 is connected to the communication hole 16 of the outer cylinder 10 via a tube 61. The tube 61 is attachable and detachable with respect to the outer cylinder 10. A staining solution is injected from the syringe 60 through the tube 61 into the chamber P. In addition to the staining solution, a fixing solution that fixes the cells on the slide 40 may be injected from the syringe 60 into the chamber P.

As illustrated in FIG. 1, the tubular part 22 of the inner cylinder 20 is inserted into the through hole 14 of the outer cylinder 10. Specifically, an inner diameter L3 of the through hole 14 in the direction perpendicular to the longitudinal axis direction of the outer cylinder 10 illustrated in FIG. 2 is larger than an outer diameter L2 of the tubular part 22 illustrated in FIG. 3. The difference between the inner diameter L3 and the outer diameter L2 is slight. As illustrated in FIG. 1, when the tubular part 22 of the inner cylinder 20 is inserted into the through hole 14 of the outer cylinder 10, the O-ring 25 is pressed and the O-ring 25 is brought into an urged state in the through hole 14. That is, the liquid tightness of the space P1 surrounded by the through holes 14 of the inner cylinder 20 and the outer cylinder 10 is ensured by the O-ring 25.

Additionally, the tubular part 22 of the inner cylinder 20 is capable of entering the through hole 14 of the outer cylinder 10 until the upper part 21 of the inner cylinder 20 having an enlarged diameter abuts against the recess 11b of the upper part 11 of the outer cylinder 10. In this abutment state, the filter 24 and the slide 40 are placed at a distance. A distance D from the filter 24 to the slide 40 may be such that the inner cylinder 20 does not block the communication hole 16, and is, for example, 3 mm or more and less than 5 mm. Moreover, in this abutment state, since the communication hole 16 is located in the step part 27, the liquid that has passed through the communication hole 16 is injected into the space P1.

As illustrated in FIG. 1, the cell inspection device 1 includes an observation unit 50. When the base plate 30 is fitted to the stage (not illustrated) of the microscope, the observation unit 50 is capable of being inserted into the observation hole 32. The observation unit 50 is movable in a direction in which the observation unit approaches or separates from the slide 40. As the observation unit 50 approaches or separate from the slide 40, it is possible to form a focus on the cells.

The cell inspection device 1 further includes a monitor (not illustrated). The monitor is connected to the observation unit 50. An image of the cells acquired by the observation unit 50 is displayed on the monitor.

Figure 6:
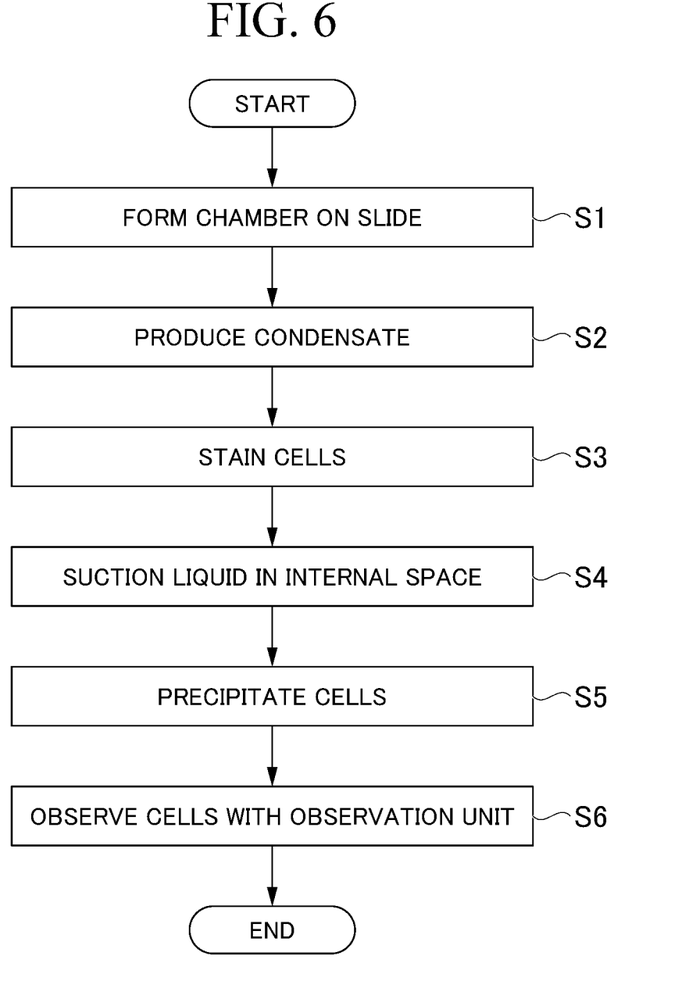
FIG. 6 is a flowchart illustrating a cell inspection method of the present invention.

Next, a cell inspection method according to the present embodiment will be described with reference to a flowchart of FIG. 6.

First, as illustrated in FIG. 5, the outer cylinder 10 is fixed to the base plate 30 with screws 33 to form the chamber P (preparation step: Step S1). The base plate 30 to which the outer cylinder 10 is fixed is fitted to the stage (not illustrated) of the microscope.

Figure 7:
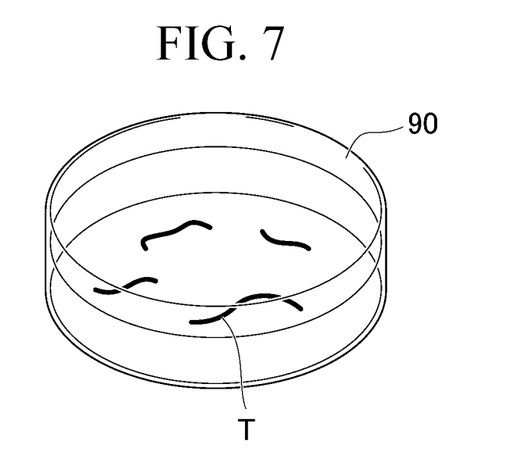
FIG. 7 is a view illustrating a procedure of producing a cell suspension used in the cell inspection method of the present invention.
Figure 8:
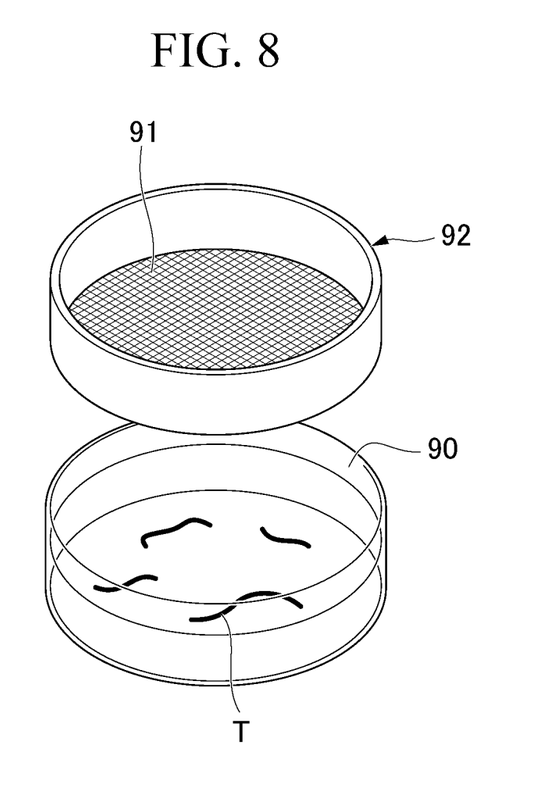
FIG. 8 is a view illustrating the procedure of producing the cell suspension used in the cell inspection method of the present invention.
Figure 9:
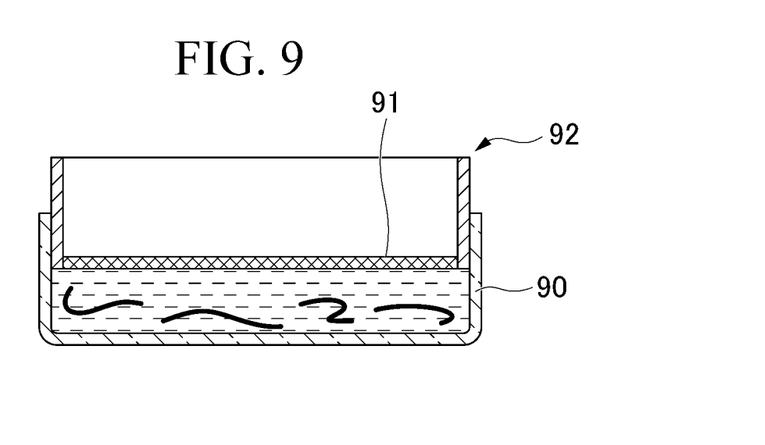
FIG. 9 is a view illustrating the procedure of producing the cell suspension used in the cell inspection method of the present invention.
Figure 10:
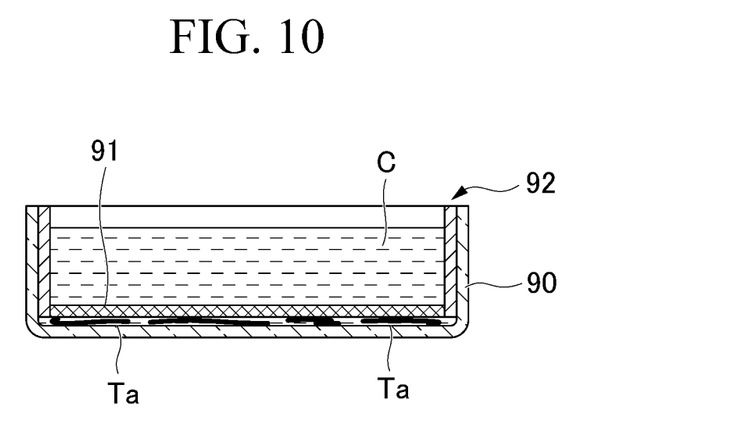
FIG. 10 is a view illustrating the procedure of producing the cell suspension used in the cell inspection method of the present invention.

Next, while the inside of a patient's body is observed with an ultrasound endoscope, a puncture needle or the like is inserted into the tissue to collect cells. As illustrated in FIG. 7, the collected cells T are discharged into a petri dish 90, and a cell preservation solution is injected into the petri dish 90 to loosen the cells T. After the cells T are loosened, as illustrated in FIG. 8, a container 92 having a filter 91 provided at a bottom part thereof is inserted into the petri dish 90. As illustrated in FIG. 9, when the container 92 is pushed into the petri dish 90, a cell suspension C in the container 92 and cells Ta in the petri dish 90 are separated as illustrated in FIG. 10. In this way, the cell suspension C is produced.

Figure 11:
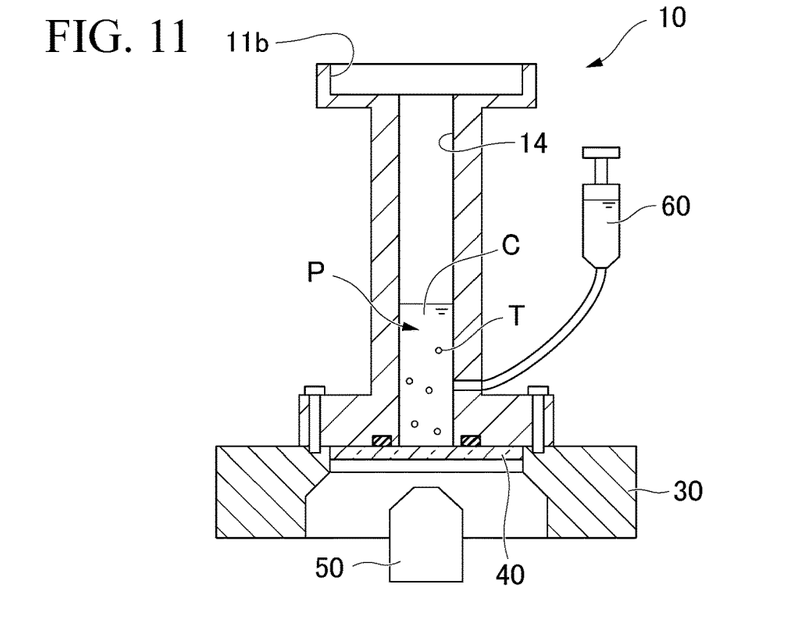
FIG. 11 is a view illustrating the cell inspection method of the present invention.

The produced cell suspension C is suctioned into a dropper, a syringe, or the like, and injected from the recess 11b of the outer cylinder 10. As illustrated in FIG. 11, as the cell suspension C, the cell suspension C containing the cells T is stored in the chamber P.

Figure 12:
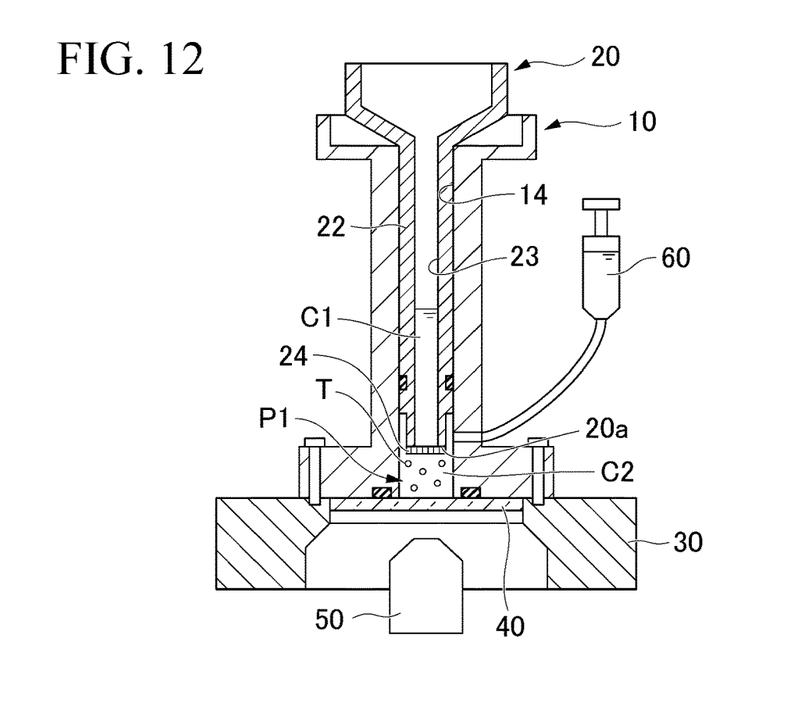
FIG. 12 is a view illustrating the cell inspection method of the present invention.

Next, as illustrated in FIG. 12, the inner cylinder 20 enters the through hole 14 of the outer cylinder 10 from the bottom surface 20a. When the tubular part 22 of the inner cylinder 20 is pushed forward, the filter 24 is provided on the bottom surface 20a of the inner cylinder 20. Thus, the liquid C1 other than the cells T passes through the filter 24 and flows into the internal space 23 of the tubular part 22, and a cell concentrate C2 containing the cells T remains in the space P1. In this way, the cell concentrate C2 is produced (concentrate production step: Step S2). Although the tubular part 22 of the inner cylinder 20 may be pushed into the through hole 14 of the outer cylinder 10 only once, the inner cylinder 20 may be advanced and retracted several times in the longitudinal axis direction of the outer cylinder 10. By advancing and retracting the inner cylinder 20 with respect to the outer cylinder 10, the cell concentrate C is produced faster.

Figure 13:
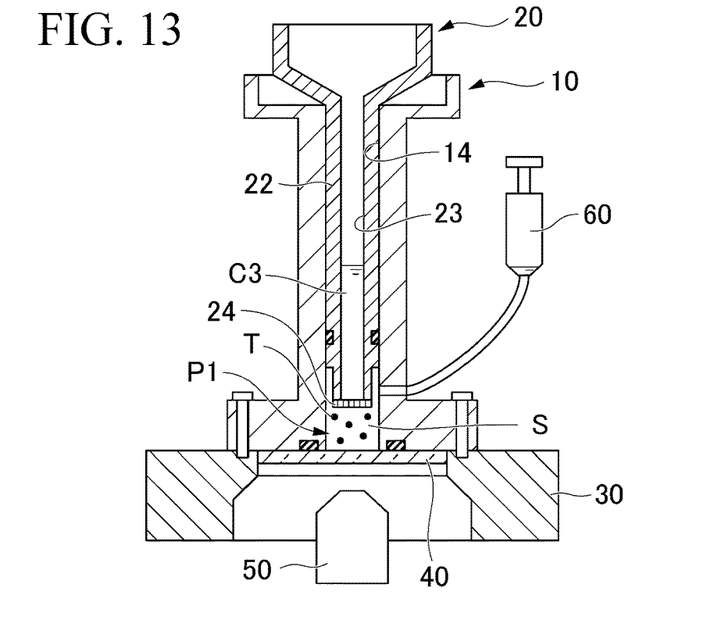
FIG. 13 is a view illustrating the cell inspection method of the present invention.

Next, the staining solution S is injected from the syringe 60 through the tube 61 and the communication hole 16 into the cell concentrate C2 in the space P1. As illustrated in FIG. 13, the staining solution S stays in the space P1 and the cells T are stained (staining step: Step S3). In a case where the step part 27 is not formed in the tubular part 22 of the inner cylinder or in a case where the communication hole 16 is blocked, the inner cylinder 20 is pulled up once and then the staining solution is injected. The inner cylinder 20 may be advanced and retracted several times in the longitudinal axis direction of the outer cylinder 10. By advancing and retracting the inner cylinder 20 with respect to the outer cylinder 10, the cells T are stained faster. When the staining solution is injected into the space P1, the liquid C1 in the internal space 23 and the staining solution S are mixed with each other and a colored liquid C3 is stored in the internal space 23.

Figure 14:
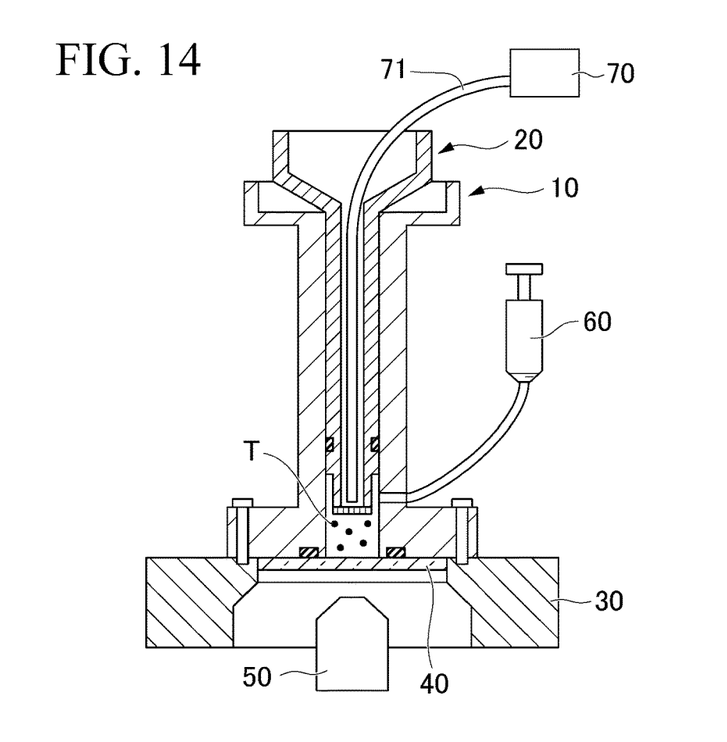
FIG. 14 is a view illustrating a cell inspection method of the present invention.

Next, as illustrated in FIG. 14, the liquid C3 is discharged to the outside of the internal space 23. The method for discharging the liquid C3 is not particularly limited, but the liquid C3 is discharged by, for example, an aspirator 70. The aspirator 70 has a tube 71 capable of being inserted into the internal space 23. That is, the outer diameter of the tube 71 is smaller than the inner diameter of the internal space 23. The tube 71 is inserted into the internal space 23, and the liquid C3 in the internal space 23 is suctioned and discharged (suction step: Step S4).

Figure 15:
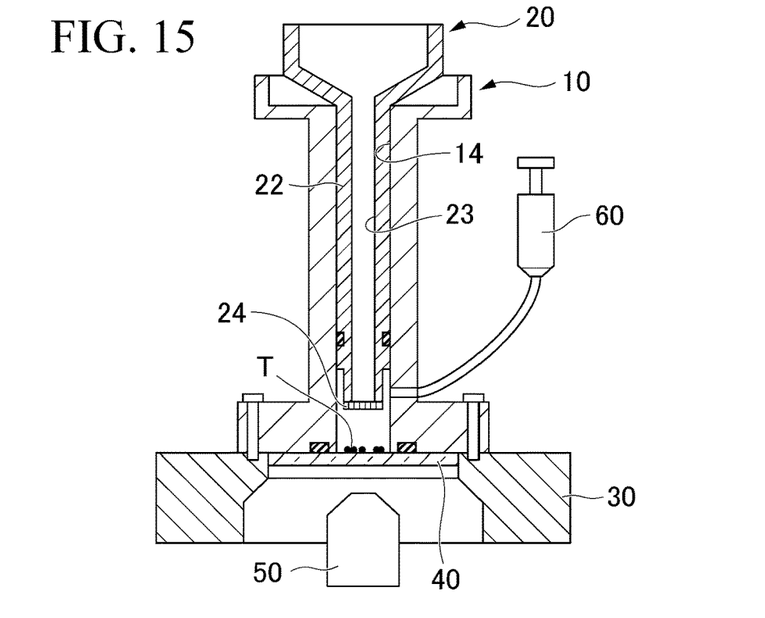
FIG. 15 is a view illustrating the cell inspection method of the present invention.

As illustrated in FIG. 15, the stained cells T precipitates on the slide 40 after a while (cell precipitation step: Step S5).

Figure 16:
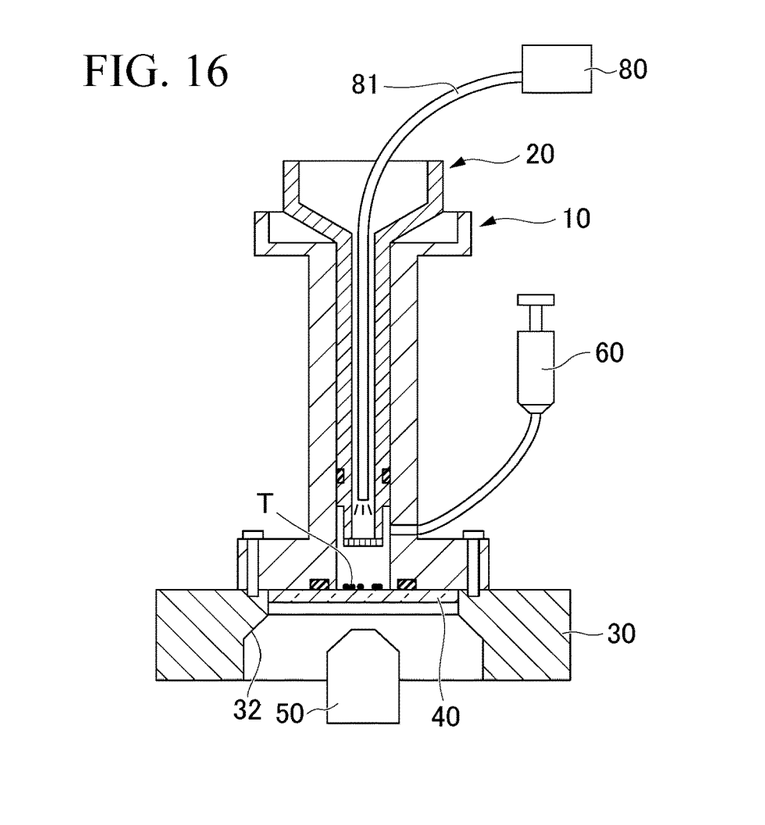
FIG. 16 is a view illustrating the cell inspection method of the present invention.

Next, as illustrated in FIG. 16, the cells T are irradiated with light by using a light source 80 having an optical fiber 81. The optical fiber 81 is insertable through the internal space 23. That is, the outer diameter of the optical fiber 81 is smaller than the inner diameter of the internal space 23. The optical fiber 81 is inserted into the internal space 23, and while the light source 80 emits the light, the observation unit 50 observes the cells T on the slide 40 with the monitor (not illustrated) (observation Step: Step S6). As necessary, the observation unit 50 enters the observation hole 32 and brought closer to the slide 40. When the required cells have been collected, the cells Ta illustrated in FIG. 10 are conveyed to the pathological inspection. On the other hand, in a case where the required cells have not been collected, the cells are collected again using the endoscope.

According to the cell inspection device 1 of the present embodiment, the cell concentrate C2 is produced by inserting the tubular part 22 of the inner cylinder 20 through the through hole 14 of the outer cylinder 10. Accordingly, more cells T can be secured on the slide 40.

Additionally, since the communication hole 16 for injecting the staining solution S is provided on an outer wall 13a of the tubular part 22, the communication hole 16 does not hinder the observation by the observation unit 50.

Since the cell inspection device 1 includes the base plate 30 on which the slide 40 is mounted, the outer cylinder 10 and the slide 40 can be fixed. Accordingly, the cells T can be more stably observed.

Since the cell inspection device 1 includes the optical fiber 81 (light source) capable of being inserted into the internal space 23 of the inner cylinder 20, the cells T can be clearly observed.

Since the filter 24 is made of a material having a refractive index higher than that of the cell suspension C, the light emitted from the light source 80 can be diffused. Accordingly, the light emitted from the light source 80 can be efficiently used.

According to the cell inspection method of the present embodiment, the preparation step (Step S1), the concentrate production step (Step S2), the staining step (Step S3), the cell precipitation step (Step S5), and the observation step (Step S6) are perform on the stage of the microscope, that is, in the same location. Therefore, the cells T can be smoothly and rapidly examined.

Since the filter 24 of the inner cylinder 20 is placed at a distance from the slide 40, it is possible to prevent the filter 24 from being reflected when the cells T is observed by the observation unit 50.

Since the communication hole 16 for injecting the staining solution S is formed in the outer wall 13a of the outer cylinder 10, the syringe 60 that stores the staining solution S does not hinder the observation by the observation unit 50.

Since the base plate 30 is only fitted to the stage of a generally used microscope and the tube 61 of the syringe 60 is attachable and detachable with respect to the outer cylinder 10, the base plate 30, the outer cylinder 10, and the inner cylinder 20 can be configured as a disposable type replaced for each use. In addition, the base plate 30 can be reused by removing the screws 33.

Here, the amount (area) of cells secured on the slide 40 when an inner cylinder having no filter 24 provided on the bottom surface 20a was used and the amount (area) of cells secured on the slide 40 when the inner cylinder 20 having the filter 24 of the present embodiment was used were compared with each other. The start time was when the cell suspension C was injected into the chamber P, and the area of cells on the slide 40 a after 3 minutes passed in a case where an inner cylinder with no filter was used as it is and the area of cells on the slide 40 after 3 minutes including the time for pushing the tubular part 22 of the inner cylinder 20 into the through hole 14 of the outer cylinder 10 passed in a case where the inner cylinder 20 having the filter 24 was used were compared with each other. As a result, that is, the area of the inner cylinder 20 having the filter 24 was about 4.7 times larger than that in a case where the inner cylinder without the filter was used. That is, according to the cell inspection device 1 and the cell inspection method of the present embodiment, it was found that required cells can be precipitated on the slide 40 in a shorter time than in the related art.

Additionally, after the concentrate production step of Step S2, the amount (area) of cells in a case where the slide 40 was removed from the base plate 30 and immersed in the staining solution and the amount (area) of cells stained by the cell inspection device 1 of the present embodiment were compared with each other. As a result, the area in the case where the area of the inner cylinder 20 having the filter 24 was about 3.5 times larger than that in the case where the inner cylinder without the filter was used. That is, according to the cell inspection device 1 and the cell inspection method of the present embodiment, it was found that cells can be prevented from falling out into the staining solution.

Figure 17:
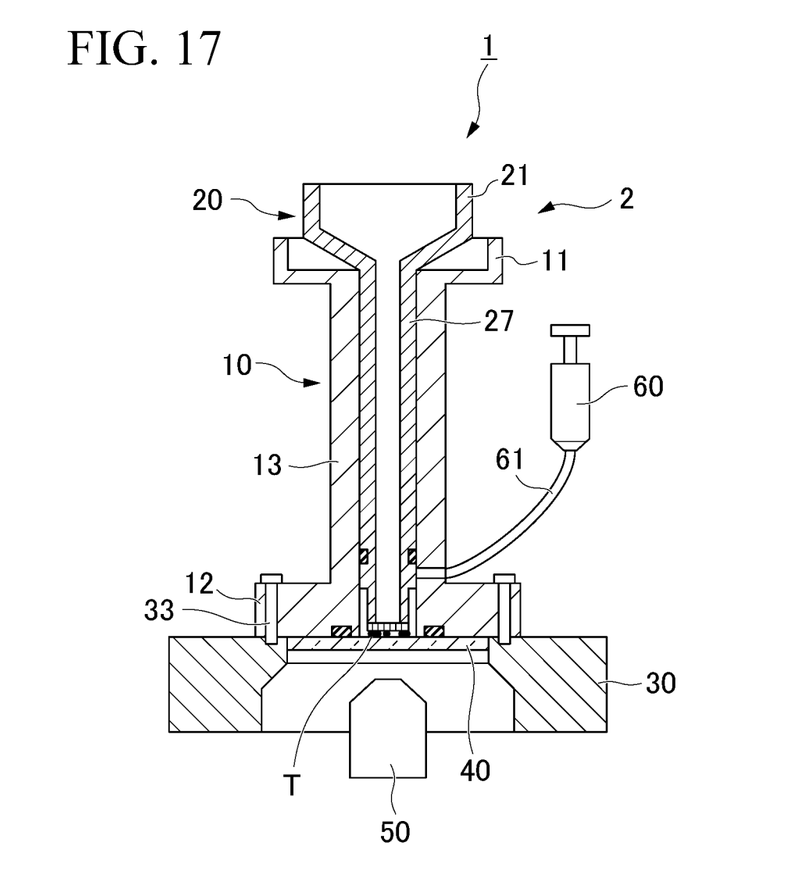
FIG. 17 is an overall view illustrating a modification example of the cell inspection device according to the embodiment of the present invention.

In addition, although the filter 24 of the inner cylinder 20 is placed at a distance from the slide 40, as illustrated in the modification example of FIG. 17, the tubular part 22 may be longer than the tubular part 22 of the present embodiment in the longitudinal axis direction of the inner cylinder 20, and the filter 24 of the inner cylinder 20 may be brought into contact with the slide 40. Accordingly, the cells T can be fixed on the slide 40.

Figure 18:
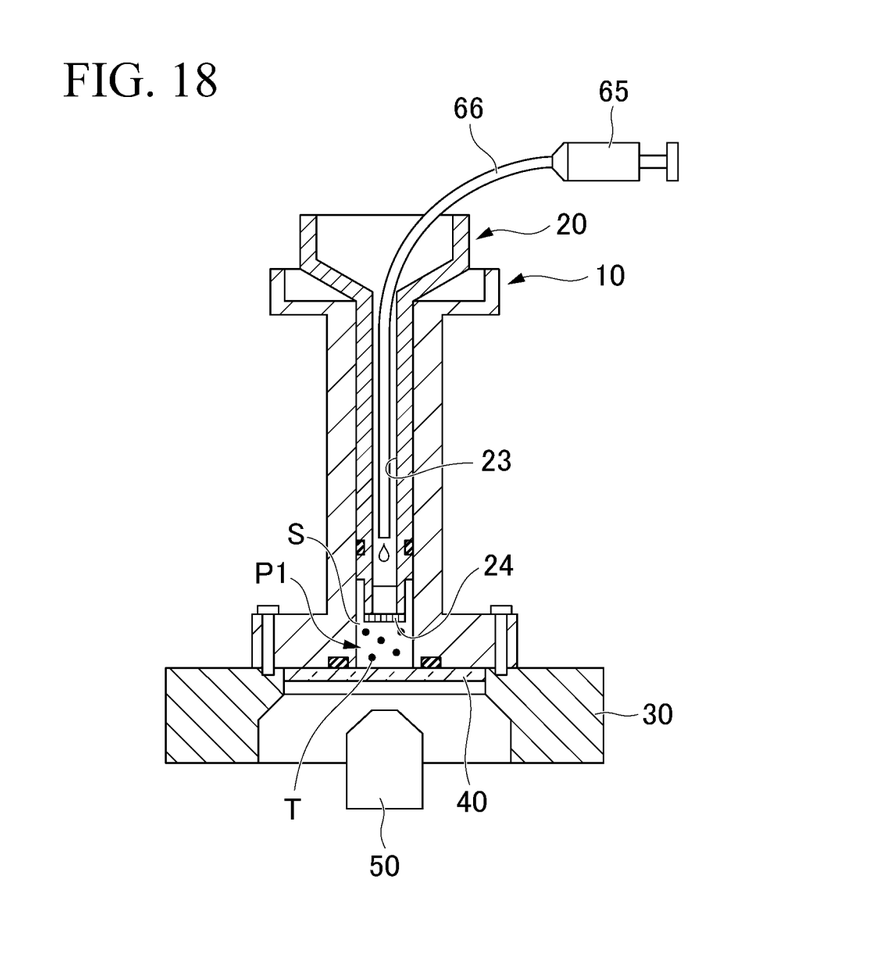
FIG. 18 is an overall view illustrating a modification example of the cell inspection device according to the embodiment of the present invention.

Additionally, although the communication hole 16 is formed in the tubular part 13, a communication hole for allowing the through hole 14 and the outside to communicate with each other may be formed in the bottom part 12 of the outer cylinder 10. Additionally, the outer cylinder 10 may not be provided with the communication hole 16, and as illustrated in FIG. 18, the tube 66 provided in the syringe 65 may be inserted into the internal space 23 of the inner cylinder 20, and the staining solution S may be injected from the internal space 23 through the filter 24 into the space P1.

Additionally, although the filter 24 is made of a material having a refractive index higher than that of the cell suspension, the filter 24 may not be necessarily made of a material having a refractive index higher than that of the cell suspension.

Although the outer cylinder 10 is configured to include the upper part 11, the bottom part 12, and the tubular part 13, the outer cylinder 10 may be configured to include at least the tubular part 13 having the through hole 14.

Although the outer cylinder 10 is fixed to the base plate 30 with the screws 33, the fixing between the outer cylinder 10 and the base plate 30 is not limited to this. Additionally, the outer cylinder 10 may only be mounted on the base plate 30.

Additionally, the cell inspection method does not necessarily need to include the suction step (Step S4) of discharging the liquid C3 to the outside of the internal space 23. However, since the liquid C3 is colored, the light from the optical fiber 81 can be more efficiently used in a case where the liquid C3 is not present in the internal space 23. For example, the inner cylinder 20 may be taken out from the outer cylinder 10, the inner cylinder 20 may be turned upside down, and the liquid C3 in the internal space 23 may be discharged.

Additionally, although the image of the cells T acquired by the observation unit 50 was observed on the monitor (not illustrated), the cells T may be visually observed.

Although preferred embodiments of the present invention have been described above, the present invention is not limited to these embodiments. Additions, omissions, substitutions, and other modifications of the components can be made without departing from the spirit of the present invention. The present invention is limited not by the aforementioned description but only by the scope of the attached claims.

According to the cell inspection device and cell inspection method of each of the above embodiments, since cells are stained and observed with a microscope while the cells are stored on the filter, the cells can be reliably secured and the cells can be smoothly and rapidly inspected. The present invention can also be applied to the inspection of bacteria by reducing the pore size of the filter.

What is claimed is:

1. A cell inspection method for inspecting cells contained in a cell suspension by using a light source and an observation unit, the cell inspection method comprising:
   a concentrate production step of injecting the cell suspension into a chamber formed of an outer cylinder and a slide, and producing a cell concentrate, the outer cylinder having a through hole;
   a staining step of staining the cells on the slide;
   a cell precipitation step of precipitating the cells on the slide; and
   an observation step of observing the cells on the slide by the observation unit while illuminating the cells with the light source,
   wherein in the concentrate production step, the cell concentrate is produced by causing an inner cylinder which has a filter provided on a bottom surface to enter from the bottom surface side into the through hole of the outer cylinder and bringing the inner cylinder closer to the slide, the inner cylinder having an internal space, and
   in the observation step, observation is performed in a state where the inner cylinder is entered into the outer cylinder.

2. The cell inspection method according to claim 1,
wherein in the staining step, the cells in the cell concentrate are stained by injecting a staining solution into a space surrounded by the inner cylinder and the through hole of the outer cylinder.

3. The cell inspection method according to claim 2, further comprising:
   a suction step of suctioning the staining solution in the internal space of the inner cylinder.

4. The cell inspection method according to claim 1,
wherein in the observation step, the filter of the inner cylinder is placed at a distance from the slide.

5. The cell inspection method according to claim 4,
wherein in at least one of the concentrate production step and the staining step, the inner cylinder is advanced and retracted in a longitudinal direction of the outer cylinder.

6. The cell inspection method according to claim 1,
wherein in the observation step, the filter of the inner cylinder is brought into contact with the slide.

7. The cell inspection method according to claim 6,
wherein in at least one of the concentrate production step and the staining step, the inner cylinder is advanced and retracted in a longitudinal direction of the outer cylinder.

8. A cell inspection device that inspects cells contained in a cell suspension, comprising:
   an outer cylinder which has a through hole and is arranged on the slide, the through hole of the outer cylinder and a slide forming a chamber;
   an inner cylinder that has an internal space, and is capable of being inserted into the through hole of the outer cylinder, a filter being provided on a bottom surface of the inner cylinder;
   a staining solution injector which injects a staining solution into the chamber in a state where the cells is concentrated; and
   an observation unit that is provided on a side opposite to a side in which the outer cylinder is provided with respect to the slide,
   wherein in a state where the cell suspension is accommodated in the chamber, a concentration of the cells is executed in a state where the inner cylinder is entered from the bottom surface side into the through hole of the outer cylinder and approaches the slide and
   in a state where the cells are stained by the staining solution and precipitated on the slide, observation of the cells by the observation unit is capable of being executed in a state where the inner cylinder is kept as entering into the outer cylinder.

9. The cell inspection device according to claim 8,
wherein a communication hole is provided in a side wall of the outer cylinder, and
the through hole of the outer cylinder and an outside communicate with each other through the communication hole.

10. The cell inspection device according to claim 8, further comprising:
    a light source which is capable of being inserted into the internal space of the inner cylinder.

11. The cell inspection device according to claim 8,
wherein the filter is made of a material having a refractive index higher than that of the cell suspension.

12. The cell inspection device according to claim 8,
wherein the filter has a pore size smaller than that of the cells.

13. A cell inspection device that inspects cells contained in cell suspension,
comprising:
    a base plate;
    an outer cylinder that has a through hole and is arranged on a slide;

an inner cylinder that has an internal space, and is capable of being inserted into the through hole of the outer cylinder, a filter being provided on a bottom surface of the inner cylinder; and a light source; and an observation unit that is provided opposite to a side in which the outer cylinder is provided with respect to the slide, wherein a chamber for injecting the cell suspension is formed by the slide and the through hole of the outer cylinder, the base plate has an observation hole formed therein and has a depression on which the slide is mounted, and the filter of the inner cylinder is made of a light-transmitting material, and the light source illuminates cells in the chamber in a state where the inner cylinder is entered into the outer cylinder.

14. The cell inspection device according to claim 13, wherein a communication hole is provided in a side wall of the outer cylinder, and the through hole of the outer cylinder and an outside communicate with each other through the communication hole.

15. The cell inspection device according to claim 13, wherein the observation unit is capable of being inserted into the observation hole.

16. The cell inspection device according to claim 13, wherein the filter is made of a material having a refractive index higher than that of the cell suspension.

17. The cell inspection device according to claim 13, wherein the filter has a pore size smaller than that of the cells.

* * * * *